US00PP18250P2

(12) United States Plant Patent
Bergman

(10) Patent No.: US PP18,250 P2
(45) Date of Patent: Nov. 27, 2007

(54) ***HIBISCUS* PLANT NAMED 'TYE-DYE WIND'**

(50) Latin Name: *Hibiscus rosa-sinensis*
Varietal Denomination: Tye-Dye Wind

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 11/450,832

(22) Filed: Jun. 9, 2006

(51) Int. Cl.
*A01H 5/00* (2006.01)

(52) U.S. Cl. ..... Plt./257

(58) Field of Classification Search ..... Plt./257
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Hibiscus* plant named 'Tye-Dye Wind', characterized by its compact, upright, somewhat outwardly spreading, uniform, dense and symmetrical plant habit that is appropriate for container production; glossy dark green-colored leaves; uniform, freely and early flowering habit; large mottled light red and pink-colored flowers; good resistance to flower bud abscission during shipping; and lack of susceptibility to pathogens common to *Hibiscus*.

2 Drawing Sheets

Botanical designation: *Hibiscus rosa-sinensis.*
Cultivar denomination: 'Tye-Dye Wind'.

BACKGROUND OF THE INVENTION

The present invention relates to a new and distinct cultivar of *Hibiscus,* botanically known as *Hisbiscus rosa-sinensis,* and hereinafter referred to by the name 'Tye-Dye Wind'.

The new *Hibiscus* is a product of a planned breeding program conducted by the Inventor in Alva, Fla. The objective of the breeding program is to create new freely-branching *Hibiscus* cultivars with a dense, uniform and compact plant habit appropriate for container production, early and uniform flowering, numerous flowers per lateral branch, desirable flower color and good postproduction longevity.

The new *Hibiscus* originated from a cross-pollination made by the Inventor in Alva, Fla. in early 1999, of the *Hibiscus rosa-sinensis* cultivar Captiva Wind, disclosed in U.S. Plant patent application Ser. No. 10/156,544, as the female, or seed, parent with a proprietary *Hibiscus rosa-sinensis* selection, designated as code number YB-1715, not patented, as the male, or pollen, parent. The cultivar 'Tye-Dye Wind' was discovered and selected by the Inventor as a flowering plant within the progeny of the stated cross-pollination in a controlled environment in Alva, Fla. on Sep. 6, 2000.

Asexual reproduction of the new *Hibiscus* by vegetative terminal cuttings in a controlled environment in Alva, Fla. since February, 2001, has shown that the unique features of this new *Hibiscus* are stable and reproduced true to type in successive generations.

SUMMARY OF THE INVENTION

The cultivar 'Tye-Dye Wind' has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Tye-Dye Wind'. These characteristics in combination distinguish 'Tye-Dye Wind' as a new and distinct cultivar of *Hibiscus:*

1. Compact, upright, somewhat outwardly spreading, uniform, dense and symmetrical plant habit that is appropriate for container production.
2. Glossy dark green-colored leaves.
3. Uniform, freely and early flowering habit.
4. Large mottled light red and pink-colored flowers.
5. Good resistance to flower bud abscission during shipping.
6. Not susceptible to pathogens common to *Hibiscus* grown under Florida production conditions.

Plants of the new *Hibiscus* can be compared to plants of the female parent, the cultivar Captiva Wind. Plants of the new *Hibiscus* differ from plants of the cultivar Captiva Wind in the following characteristics:

1. Plants of the new *Hibiscus* have leaves with entire margins whereas plants of the cultivar Captiva Wind have deeply-lobed leaves.
2. Plants of the new *Hibiscus* and the cultivar Captiva Wind differ in flower coloration as plants of the cultivar Captiva Wind have lavender-colored flowers with pink-colored margins.

Plants of the new *Hibiscus* can be compared to plants of the male parent, the proprietary *Hibiscus* selection code number YB-1715. Plants of the new *Hibiscus* differ from plants of the male parent selection in the following characteristics:

1. Plants of the new *Hibiscus* have smaller flowers than plants of the male parent selection.
2. Plants of the new *Hibiscus* and the male parent selection differ in flower coloration as plants of the male parent selection have creamy white-colored flowers.

Plants of the new *Hibiscus* can be compared to plants of the *Hibiscus rosa-sinensis* cultivar Belize Breeze, disclosed in U.S. Plant Pat. No. 17,492. In side-by-side comparisons conducted in Alva, Fla., plants of the new *Hibiscus* differed from plants of the cultivar Belize Breeze in the following characteristics:

1. Plants of the new *Hibiscus* had leaves with entire margins whereas plants of the cultivar Belize Breeze had lobed leaves.
2. Plants of the new *Hibiscus* had smoother petal margins than plants of the cultivar Belize Breeze.
3. Flowers of plants of the new *Hibiscus* and the cultivar Belize Breeze differed in flower color as plants of the cultivar Belize Breeze had bright pink-colored flowers.

BRIEF DESCRIPTION OF THE PHOTOGRAPHS

The accompanying colored photographs illustrate the overall appearance of the new *Hibiscus,* showing the colors as true as it is reasonably possible to obtain in colored reproductions of this type. Colors in the photographs may differ slightly from the color values cited in the detailed botanical description which accurately describe the colors of the new *Hibiscus*.

The photograph on the first sheet comprises a side perspective view of typical flowering plants of 'Tye-Dye Wind' grown in a container.

The photograph on the second sheet comprises a close-up view of a typical flower and leaves of 'Tye-Dye Wind'.

DETAILED BOTANICAL DESCRIPTION

The photographs and following observations, measurements and values describe plants grown in Alva, Fla. in 15-cm containers in polycarbonate-covered greenhouses during the spring under conditions which closely approximate commercial production. During the production of the plants, day temperatures ranged from about 16° C. to about 37° C. and night temperatures ranged from about 7° C. to about 26° C. Plants were about four months old when the photographs and the description were taken. In the description, color references are made to The Royal Horticultural Society Colour Chart, 1995 Edition, except where general terms of ordinary dictionary significance are used.

Botanical classification: *Hibiscus rosa-sinensis* cultivar 'Tye-Dye Wind'.

Parentage:

*Female, or seed, parent.*—*Hibiscus rosa-sinensis* cultivar Captiva Wind, disclosed in U.S. Plant patent application Ser. No. 10/156,544.

*Male or pollen parent.*—Proprietary selection of *Hibiscus rosa-sinensis* designated as code number YB-1715, not patented.

Propagation:

*Type.*—By vegetative terminal cuttings.

*Time to initiate roots.*—About 10 days at temperatures of 24° C.

*Time to develop roots.*—About four weeks at temperatures of 24° C.

*Root description.*—Thick, fibrous; white in color.

*Rooting habit.*—Somewhat freely branching; moderately dense.

Plant description:

*Plant form and growth habit.*—Perennial, evergreen, upright, somewhat outwardly spreading, compact, uniform, dense and symmetrical plant habit. Moderately vigorous growth habit.

*Branching habit.*—Freely branching, usually about three to four lateral branches develop after removal of terminal apex.

*Plant height.*—About 34 cm.

*Plant diameter* (*area of spread*).—About 42 cm.

Lateral branch description:

*Length.*—About 28 cm.

*Diameter.*—About 5 mm.

*Texture.*—Immature, smooth; mature, woody and rough.

*Color, immature.* Darker than 146A.

*Color, mature.*—Close to 197A tinged with close to 199A.

Foliage description:

*Arrangement.*—Alternate, single; numerous; symmetrical.

*Length.*—About 8.3 cm.

*Width.*—About 6.7 cm.

*Shape.*—Roughly ovate.

*Apex.*—Acute.

*Base.*—Obtuse to cordate.

*Margin.*—Serrate to crenate.

*Aspect.*—Concave; apex reflexed.

*Texture, upper and lower surfaces.*—Glabrous; leathery.

*Luster, upper surface.*—Glossy.

*Luster, lower surface.*—Somewhat glossy.

*Venation pattern.*—Palmate.

*Color.*—Developing foliage, upper surface: More green than 147A. Developing foliage, lower surface: More green than 146A. Mature foliage, upper surface: Darker than 147A; venation, similar to lamina. Mature foliage, lower surface: More green to 147A; midvein, close to 146A; lateral veins, similar to lamina.

*Petiole.*—Length: About 3.5 cm. Diameter: About 4 mm. Texture, upper and lower surfaces: Slightly pubescent. Color, upper and lower surfaces: Close to 147A.

Flower description:

*Flower arrangement.*—Flowers arranged singly at terminal leaf axils. Uniform and freely flowering habit with usually about three or four flower buds and/or open flowers per terminal apex. Flowers face mostly upright.

*Flower appearance.*—Rounded, mottled light red and pink-colored flowers. Flowers are open for about one day. Flowers persistent.

*Natural flowering season.*—Usually spring and summer or during periods of warm weather.

*Flower diameter.*—About 12 cm.

*Flower length* (*height*).—About 8 cm.

*Flower bud* (*just before showing color*).—Resistance to abscission during shipping: Plants of the new *Hibiscus* have been observed to resist flower bud drop when stored in a closed box for five days at 13° C. Rate of opening: About one or two days depending on temperatures. Length: About 2.5 cm. Diameter: About 1.5 cm. Shape: Oblong. Color: Close to 147A.

*Petals.*—Arrangement: Corolla consists of five petals that are fused at base; petals imbricate. Length: About 7 cm. Width: At widest point, about 6.5 cm; at base, about 5 mm. Shape: Spatulate. Apex: Rounded. Base: Attenuate. Margin: Entire; slightly undulate. Texture: Upper surface: Smooth, glabrous, satiny. Lower surface: Glabrous; somewhat rugose.

Color: When opening and fully opened, upper surface: Close to 55B mottled with 52A to 54A to 54B. When opening and fully opened, lower surface: Close to 55C to 155B.

*Sepals.*—Appearance: Five sepals fused into a tubular star-shaped calyx. Length: About 2.5 cm. Width: About 1.1 cm. Shape: Lanceolate. Apex: Sharply acute. Margin: Entire. Texture, upper surface: Smooth; waxy. Texture, lower surface: Pubescent. Color, upper surface: Close to 144A. Color, lower surface: Close to 146A.

*Bracts.*—Appearance: About seven fused at base. Length: About 1.6 cm. Width: About 1.4 mm. Shape: Linear. Apex: Acute. Margin: Entire. Texture, upper surface: Smooth, glabrous. Texture, lower surface: Sparsely pubsecent. Color, upper and lower surfaces: Close to 147A.

*Peduncles.*—Length: About 5.7 cm. Diameter: About 3 mm. Angle: Slightly bent towards the flower. Strength: Strong, flexible. Texture: Pubescent. Color: More green than 146A.

*Reproductive organs.*—Androecium: Stamen number: Numerous, about 65. Filament length: About 4 mm. Filament color: Close to 52A. Anther shape: Reniform. Anther size: About 2 mm by 1 mm. Anther color: Close to 13D. Amount of pollen: Moderate. Pollen color: Close to 13A. Gynoecium: Pistil length: About 7.2 cm. Pistil diameter: Towards the apex, about 3 mm; towards the base, about 7 mm. Style texture: Smooth, waxy. Style color: Towards the apex, close to 52A; towards the base, close to 50D. Stigma appearance: Five, rounded. Stigma diameter: About 2 mm. Stigma color: 45A. Ovary color: Close to 154D.

*Seed/fruit.*—Seed and fruit production has not been observed.

Temperature tolerance: Plants of the new *Hibiscus* have been observed to tolerate temperatures from about 0° C. to about 38° C.

Pathogen/pest resistance: Plants of the new *Hibiscus* grown under Florida production conditions have not been shown to be susceptible to pathogens common to *Hibiscus* such as Pseudomonas, Pythium and Phytophthora. Plants of the new *Hibiscus* have not been observed to be tolerant to pests and other pathogens.

It is claimed:

1. A new and distinct *Hibiscus* plant named 'Tye-Dye Wind' as illustrated and described.

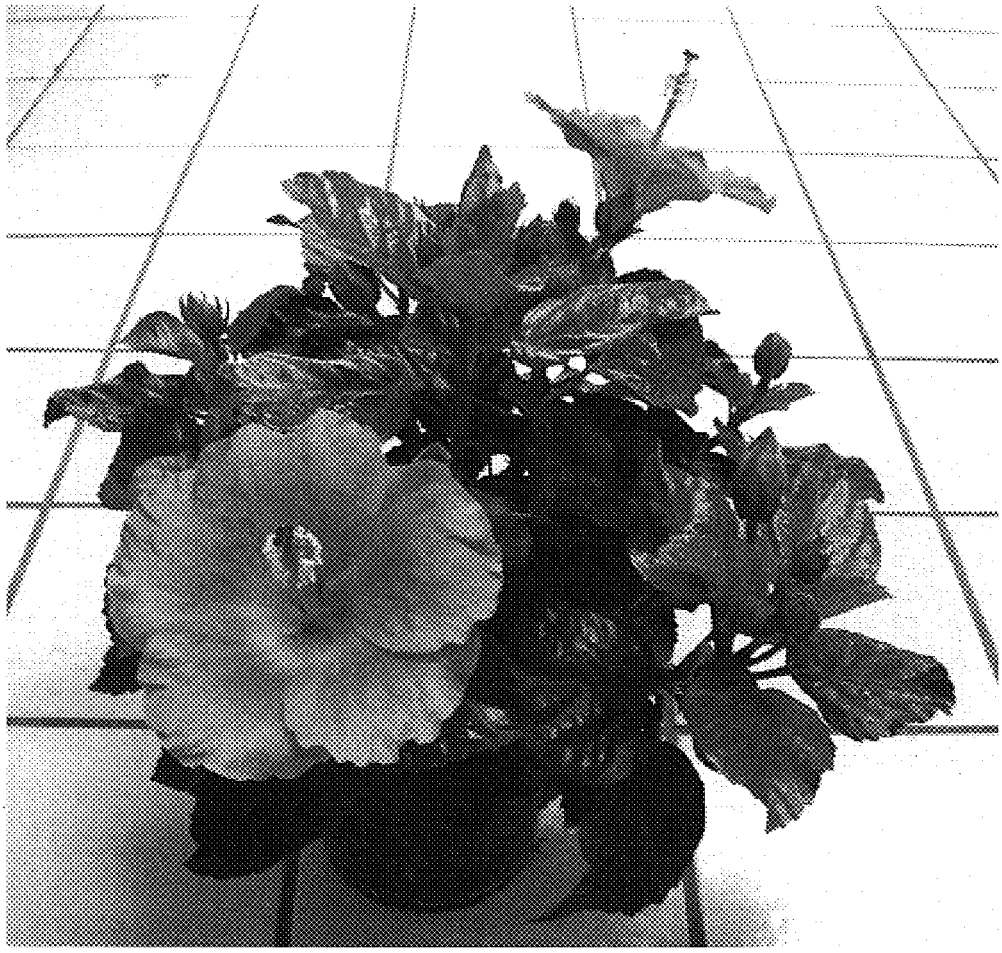

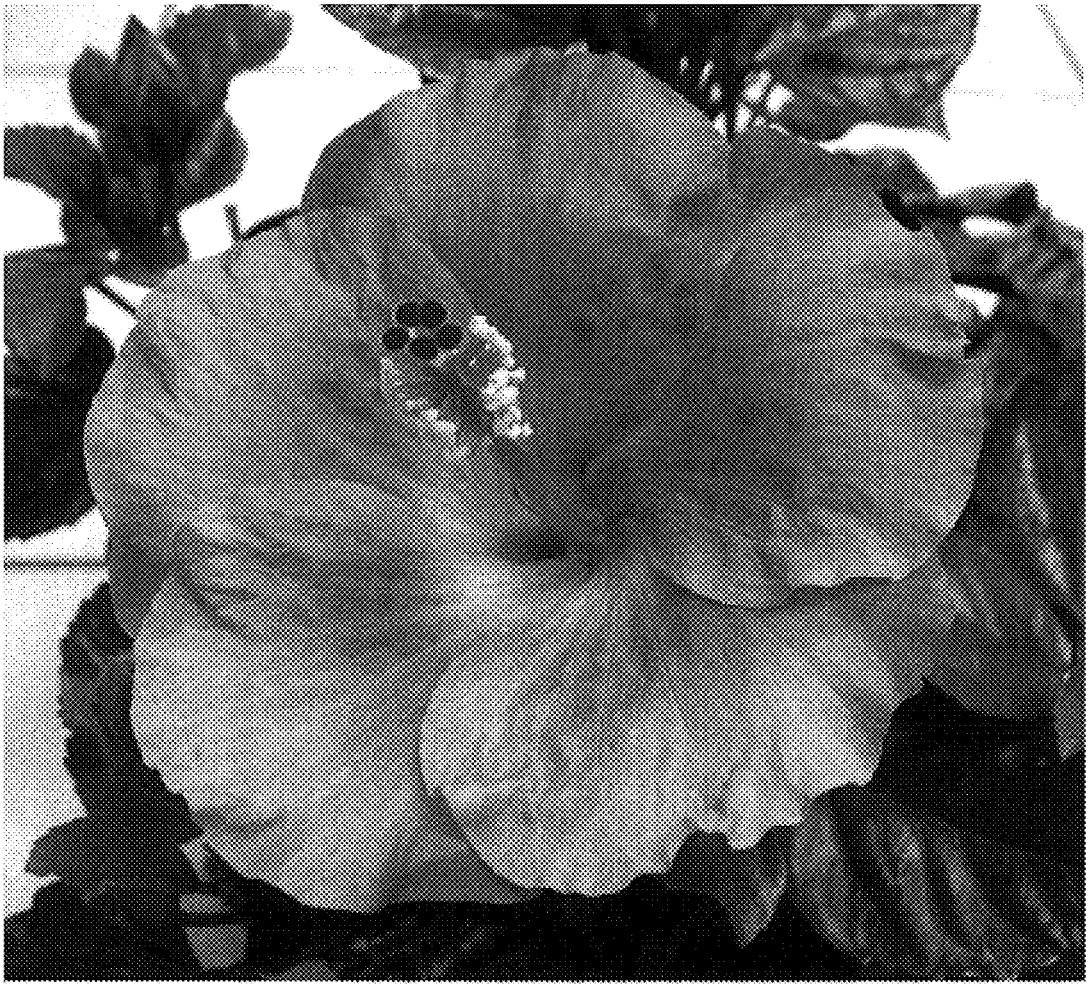

* * * * *